United States Patent [19]
Hainline

[11] Patent Number: 6,004,930
[45] Date of Patent: Dec. 21, 1999

[54] PHENYLALANINE FREE PROTEIN

[76] Inventor: Bryan E. Hainline, 1622 Nottingham Dr., Indianapolis, Ind. 46240

[21] Appl. No.: 08/674,984

[22] Filed: Jul. 3, 1996

Related U.S. Application Data

[63] Continuation of application No. 08/348,594, Dec. 2, 1994, abandoned.

[51] Int. Cl.$^6$ ............... A61K 38/00; A61K 35/78; C12N 15/00; C07H 21/00
[52] U.S. Cl. ............ 514/12; 435/172.1; 435/172.3; 514/2; 530/372; 530/373; 536/23.1
[58] Field of Search ............... 435/172.3, 172.1, 435/252.33, 255.1, 69.1; 514/12, 2; 530/372, 373; 536/23.1, 26, 27

[56] References Cited

U.S. PATENT DOCUMENTS

| | | | |
|---|---|---|---|
| 4,885,357 | 12/1989 | Larkins et al. | 530/373 |
| 4,886,878 | 12/1989 | Larkins et al. | 536/26 |

FOREIGN PATENT DOCUMENTS

0285675A1  10/1988  European Pat. Off. .

OTHER PUBLICATIONS

Berry, H.K., et al., (1976) Am. J. Clin. Nutri. 29, 351–357.
Norrander, J., et. al. (1983) Gene 26, 101–106.
Cregg, James M., Vedvick, Thomas S. and Raschkle, William C. (1993) Recent Advances in the Expression of Foreign Genes in *Pichia pastoris*. *Bio Technology* 11:905–909.
Marks, M. David and Larkins, Brian A. (1982) Analysis of Sequence Microheterogeneity among Zein Messenger RNAs. *J. Biol. Chem.* 257 (17): 9976–9983.
Scriver, Charles R., Kaufman, Seymour, Eisensmith, Randy C., and Woo, Savio L.C. (1995) The Hyperphenylalaninemias in *The Metabolic Basis of Inherited Disease*, (Scriver, C.S., et al., eds) mcGraw–Hill, Inc. New York, pp. 1015–1075.
Acosta, P., (1989) Nutrition Support of Children, Adolescents and Adults With Phenylketonuria (PKU) in *Nutrition Support Protocols*, (K.V. Sproat, C. Russell, eds.) Ross Laboratories, Columbus, pp. 9–17.
Acosta, P., Yannicelli, S. (1993) Nutrition Support of Infants, Children and Adults in *Nutrition Support Protocols*, (Cameron, A., C. Russell, eds.) Ross Laboratories, Columubus, pp. 1–16.

Prat, S. Cortads, J., Puigdomenech, P. and Palau, J. (1985) Nucleic Acid (cDNA) and Amino Acid Sequences of the Maize Endosperm Protein Glutelin–2. *Nucleic Acids Res.* 13 (5): 1493–1504.
Wang, S–Z. and Esen, A. (1986) Primary Structure of a Proline–Rich Zein and Its cDNA. *Plant Physiol.* 81: 70–74.
Thompson G.A. and Larkins B.A. (1989) Structural Elements Regulating Zein Gene Expression. *BioEssays* 10 (4): 108–113.
Osborne, T.B. (1908) Our Present Knowledge of Plant Proteins. *Science* 28 (718): 417–427.
Esen, A. (1986) Separation of Alcohol–Soluble Proteins (Zeins) from Maize into Three Fractions by Differential Solubility. *Plant Physiology* 80: 623–627.
Zein (1989) in 1990, USP XXII, NF XVII *The United States Pharmacpeia, The National Formulary*, The United States Pharmacopeial Convention, Inc., p. 1997.
Wang S. and Esen, A. (1985) Expression of Maize Prolamins in *Escherichia coli Plant Science* 42: 49–54.
Penrose, l., and Quastel, J.H. (1937) Metabolic Studies in phyenylketonuria. *Biochem J.* 31: 266–74.
Bickel, H., Gerard, J., and Hickman, E.M. (1953) Influence of Phenylalanine Intake on Phenylketonuria. *Lancet* (Oct. 17): 812–813.
Prat, Salome, Perez–Grau, Lluis and Puigdomenech, Pere (1987) Multiple Variability in the Sequence of a Family of Maize Endosperm Proteins. *Gene:* 52 (1987) 41–49.
Pedersen, Karl Devereux, John, Wilson, Deborah R., Sheldon, Edward and Larkins, Brian A. (1982) Cloning and Sequence Analysis Reveal Structural Variation among Related Zein Genes in Maize. *Cell*, 29: 1015–1026.
Folling, Asbjorn (1934) Uber Ausscheidung von Phenyl-brenztraubensaure in den harn also Stoffwechselanomalie in Verbindung mit Imbezillitat, *Hoppe–Seylor's Z. Physiol–Chem.*, 227, pp. 169–176.

*Primary Examiner*—Robert A. Wax
*Assistant Examiner*—Einar Stole
*Attorney, Agent, or Firm*—Barnes & Thornburg

[57] ABSTRACT

The present invention is directed to dietary compositions for treating patients having phenylketonuria and methods for making the dietary compositions. The compositions comprise a natural protein modified to eliminate phenylalanine from the protein's amino acid sequence. These modified proteins are synthesized from genes modified to eliminate phenylalanine codons from the reading frame of the native genes.

6 Claims, 3 Drawing Sheets

| CLONE | VECTOR | INSERT SIZE | MUTATIONS |
|---|---|---|---|
| GZN0 | pGEM3Z | 5.7 kb | |
| GZN1 | pAlter-1 amp$^s$ tet$^r$ | 1.7 kb | |
| GZN10 | pAlter-1 amp$^s$ tet$^r$ | 0.83 kb | RI, RII |
| GZN12 | pAlter-1 amp$^s$ tet$^r$ | 0.83 kb | RI, FII, RII |
| MGZN2 | pAlter-1 amp$^r$ tet$^r$ | 1.7 kb | RI |
| MGZN3 | pAlter-1 amp$^r$ tet$^r$ | 1.7 kb | RII |
| MGZN4 | pAlter-1 amp$^r$ tet$^r$ | 1.7 kb | RI, RII |
| MGZN5 | pAlter-1 amp$^r$ tet$^r$ | 1.7 kb | FI |
| MGZN6 | pAlter-1 amp$^r$ tet$^r$ | 1.7 kb | FII |
| MGZN7 | pAlter-1 amp$^r$ tet$^r$ | 1.7 kb | RI, FII, RII |
| MGZN21 | pAlter-1 amp$^r$ tet$^r$ | 0.83 kb | RI, FI, RII |
| MGZN23 | pAlter-1 amp$^r$ tet$^r$ | 0.83 kb | RI, FI, FII, RII |
| EGZN20 | pET21a | 0.83 kb | RI, RII |
| EGZN21 | pET21a | 0.83 kb | RI, FI, RII |
| EGZN22 | pET21a | 0.83 kb | RI, FII, RII |
| EGZN23 | pET21a | 0.83 kb | RI, FI, FII, RII |

FIG. 2

PHENYLALANINE FREE PROTEIN

This application is a continuation of application Ser. No. 08/348,594 filed on Dec. 2, 1994, now abandoned.

FIELD OF THE INVENTION

The present invention relates to dietary therapies for minimizing the physiological symptoms of phenylketonuria in patients having phenylketonuria. More particularly, this invention is directed to a composition comprising a natural protein modified to eliminate phenylalanine from the protein's amino acid sequence, and methods for making the same.

BACKGROUND AND SUMMARY OF THE INVENTION

Phenylketonuria (PKU) is an inherited metabolic disease of humans caused by the deficiency of, or low activity of, the enzyme phenylalanine hydroxylase. Phenylalanine hydroxylase normally functions in the human body to convert the amino acid phenylalanine to tyrosine. When this enzyme is deficient, phenylalanine and its abnormal breakdown products accumulate in the bloodstream. These breakdown products are harmful to developing cells of central nervous system, resulting in symptoms of mental retardation, developmental delay, and seizures. PKU is caused by recessive mutations in a single allele in the homozygous state. About 1 in every 15,000 infants born in the United States is homozygous for this allele.

Dietary therapies have been used to effectively treat infants with PKU and prevent PKU symptoms from appearing. All states require routine tests of all newborn babies to detect PKU homozygotes. Those identified at birth are put on a special diet containing low amounts of phenylalanine. These diets provide enough phenylalanine (an essential amino acid) to supply dietary needs but not enough to permit toxic accumulations.

On the basis of 32 years of experience, it is now clear that administration of low phenylalanine diets, especially during at least the first fifteen years of life (when brain development is still in progress), allow PKU individuals to develop normally. However, PKU individuals must continue to maintain a diet low in phenylalanine throughout their entire life to avoid intellectual impairment and behavioral or psychological disorders caused by elevated blood levels of phenylalanine.

Dietary compliance of a pregnant PKU female is particularly important to ensure normal development of her child. Since phenylalanine is selectively concentrated by the placenta in the amniotic fluid of a pregnant female, maternal blood levels as low as 3–4 times normal levels can harm the developing fetus and lead to birth defects (heart and brain defects). The occurrence of birth defects arising from the mother's elevated phenylalanine levels is typically referred to as Maternal PKU Syndrome. To prevent Maternal PKU Syndrome, a PKU mother-to-be must be placed on a low phenylalanine diet prior to conception.

Dietary therapy using phenylalanine-deficient amino acid mixtures was first reported in 1953 by Bickel et al. Current treatment focuses upon the use of a low-phenylalanine diet consisting of a special metabolic formula with supplemental low-protein foods. The metabolic formulas are composed of crystalline amino acids, fats, carbohydrate sources, trace minerals and vitamins to provide a food with high amino acid content that is low or totally deficient in phenylalanine. The total dietary phenylalanine intake of a phenylketonuria individual receiving the special formulas is determined by the content of the table foods other than formula. Since dietary treatment is mandatory for the life of the individual and all high-quality protein has a substantial content of phenylalanine, intake of meats and dairy products is prohibited. Unfortunately, the administration of metabolic formulas to PKU individuals is complicated by poor palatability and odor, limited solubility of certain amino acids, and inadequate resistance to thermal degradation associated with baking or cooking.

Previous workers have altered the amino acid composition of the formulas to reduce the content of methionine and increase the amount of glutamine to improve the taste and odor, in an attempt to enhance not only the palatability of the product but also the social acceptance of medical food by family members. Other producers have also packaged the formula in fruit bar form to help disguise the taste.

The present invention solves the problem of poor palatability, taste, and processibility by utilizing an intact phenylalanine-deficient protein that supplies most of the required essential amino acids in a form (a protein) that does not have an appreciably bad taste or odor. The phenylalanine-deficient proteins of the present invention are intact natural proteins, most typically native plant proteins, that have been modified, other than by hydrolysis, to reduce or eliminate phenylalanine from the amino acid sequence of the protein. The term "intact protein" as used in accordance with the present invention is defined as an unhydrolyzed natural/native protein comprising a continuous series of amino acids linked together through peptide bonds. The term is used to distinguish the present phenylalanine deficient protein compositions over compositions comprising hydrolyzed or partially hydrolyzed proteins. The intact, modified natural proteins of the present invention may be used as a supplement in formulas or combined with protein deficient products and cooked in a manner similar to traditional foods.

Advantageously, the intact modified proteins retain many physical properties of the parent protein, including solubility characteristics, low odor and minimal taste, which allow it to be mixed into liquids, baked, or cooked in traditional mixtures. These properties make the protein products of the present invention superior to crystalline amino acid formulations, fractionated protein hydrolysis products or synthetic polypeptides.

One object of the present invention is to modify the amino acid sequence of a natural protein to reduce or eliminate phenylalanine from the amino acid sequence of the protein. These intact, modified natural proteins provide a protein supplement for use in dietary therapies for PKU patients to minimize the physiological symptoms of PKU.

An additional object of the present invention is to provide a method for synthesizing phenylalanine free protein.

Many protein sources are nutritionally incomplete in that they lack one or more of the essentials amino acids for proper nutrition of higher animals. A further object of the present invention is to increase the nutritional content of natural proteins by modifying the amino acid content of the intact protein to provide a protein that contains all the essential amino acids except phenylalanine.

BRIEF DESCRIPTION OF THE DRAWINGS

FIG. 2 lists the clones used for (ie GZN1) and generated from in vitro mutagenesis (ie MGZN2) and the clones for expressing the modified gene (ie EGZN20). GZ=gamma zein, M=mutated, E=expression vector.

DETAILED DESCRIPTION OF THE INVENTION

Figure 1:
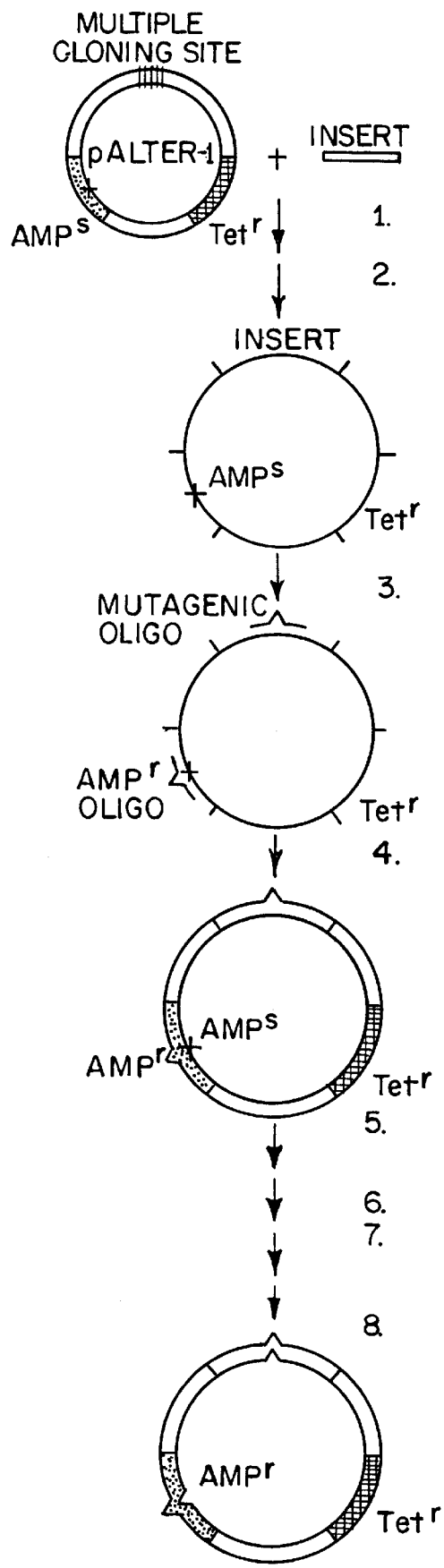
FIG. 1 is an illustration of Promega's pALTER-1 in vitro mutagenesis system. Step 1, clone insert into the pALTER vector (ampicillin sensitive, $amp^S$, tetracycline resistant, $tet^R$). Step 2, produce ssDNA in media containing tetracycline. Step 3 anneal mutagenic primer(s) and the ampicillin repair primer. Step 4, synthesize the mutant strand with T4 DNA polymerase and ligate. Step 5, transform *E. coli* BMH71-18 mutS and grow in media with ampicillin. Step 6, prepare mini-prep DNA. Step 7, transform JM109 (or DH5α) and select mutants on ampicillin plates. Step 8, screen mutants by endonuclease restriction analysis and sequence analysis.

The present invention is directed to compositions comprising novel phenylalanine-deficient proteins and methods for making the same. The novel phenylalanine-deficient compositions comprise modified natural proteins which have been modified to eliminate or reduce phenylalanine from the amino acid sequence of the protein, while retaining many of the physical properties of the parent protein. These modified proteins are more compatible for consumption by PKU individuals than the natural proteins from which they are derived. Modified natural proteins entirely free of phenylalanine are most preferred for use in dietary therapies for PKU individuals, but modified natural proteins that retain 1–3 phenylalanine residues may also be used.

In accordance with the present invention a method is provided for producing a dietary protein for consumption by PKU patients or expectant PKU mothers. The method comprises the steps of identifying a gene encoding a native protein having a relatively low content of phenylalanine; modifying the nucleic acid sequence of the gene to reduce or eliminate phenylalanine codons from the reading frame of said gene; expressing the modified gene; and isolating the expressed protein.

The genetic code consists of 64 triplet combinations (codons) which correspond to the 20 biologically important amino acids which comprise proteins. Those skilled in the art appreciate that the codons TTT and TTC encode for the amino acid phenylalanine. Thus the elimination of these two codons from the reading frame of a gene will create a modified gene encoding a phenylalanine free protein.

In one embodiment of the present invention regions of a structural gene which encode phenylalanine can be physically removed to produce a new gene which encodes a modified natural protein devoid of phenylalanine amino acids. A variety of techniques familiar to those skilled in the art can be used to remove phenylalanine coding sequences from structural genes. For example, restriction endonucleases can be used to cleave a structural gene at particular locations in the gene to create numerous nucleic acid fragments of the gene. The individual fragments of the gene can be isolated, and those fragments which encode phenylalanine amino acids can be discarded while the remaining gene fragments can be religated together to form a structural gene that encodes a modified natural protein that does not contain phenylalanine. Alternatively, the phenylalanine coding regions of the structural gene can be removed by endonuclease digestion, followed by digestion with an exonuclease (for an amount of time sufficient to remove the phenylalanine encoding nucleic acid sequences) and religation of the remaining DNA fragments.

An alternative embodiment of the present invention involves the use of site-directed mutagenesis to alter specific nucleotides of a DNA sequence to change codons encoding the amino acid phenylalanine to codons corresponding to other amino acids. Thus the codon TTT can be modified to ATT, to substitute an isoleucine for phenylalanine in the encoded protein.

These structural genes (modified by site directed mutagenesis) when introduced into a living cell will produce a modified natural protein that is devoid of the amino acid phenylalanine. These modified natural proteins will contain the same number of amino acid subunits as the corresponding natural protein, but will have amino acids other than phenylalanine located at positions occupied by phenylalanine in the natural protein.

The technique of site-directed mutagenesis employs chemically synthesizing oligonucleotides corresponding to the nucleic acid sequence whose modification is desired. The synthetic oligonucleotide is complementary to the native DNA sequence except at the exact site where a change in the coding sequence is desired. The synthetic oligonucleotide is allowed to hybridize to a single stranded DNA template comprising the nucleic acid sequence to be modified. Then the synthetic oligonucleotide is used to prime DNA synthesis of a new coding strand incorporating the desired base change.

Appropriate vectors and procedures for carrying out site-directed mutagenesis of a particular structural gene are known to those skilled in the art and are commercially available. One preferred method for altering structural genes utilizes the Altered Sites: in vitro mutagenesis system (available from Promega, Madison, Wis.).

The method for producing the phenylalanine free proteins of the present invention involves fine tuned alterations of structural genes encoding natural proteins. Since the modification of the structural genes is relatively minor, the modified proteins encoded by these genes will retain most of the physical properties of the parent protein, including size and solubility characteristics. In particular phenylalanine codons can be replaced with codons encoding similar non-polar amino acids, such as isoleucine, to minimize the impact of the modification on the physical properties of the encoded protein. Advantageously, the retention of the natural protein's physical properties allows the isolation of the modified protein using the same known procedures as used for isolating the natural protein.

Structural genes selected for modification in accordance with the present invention are preferably those genes that encode proteins that are naturally low in phenylalanine. Genes encoding natural proteins low in phenylalanine content will require fewer genetic manipulations to produce a gene encoding a phenylalanine free protein. Preferably, the natural protein will contain fewer than twelve phenylalanine amino acids and most preferably the natural protein will contain less than seven.

The seed storage proteins of plants are an example of a large group of proteins known to have a relatively low content of phenylalanine. Seed storage proteins are defined as any protein accumulated in significant quantities in developing seeds which on germination is rapidly hydrolyzed to provide a source of reduced nitrogen for the early stage of seedling growth. The natural storage proteins are present in plant cells in a highly concentrated and stable form. These proteins when modified to eliminate phenylalanine from the protein sequence are also expected to exhibit such properties. Genes encoding storage proteins have been well characterized for many diverse plants including corn, french bean, green pea, rice, sunflower, cotton, sorghum, soybean and peanut.

One preferred group of storage proteins for use in accordance with the present invention includes the zein proteins of maize (corn). Zein protein accounts for approximately 60% of total endosperm protein of maize seeds and can be grouped according to size to include the 16 and 27 kDa gamma zeins, the 22 kDa alpha zeins and the 19 kDa beta zein proteins. Zein proteins are alcohol soluble and can be purified, according to published protocols, by extraction with an alcohol solvent in the presence of a reducing agent such as 2-mercaptoethanol. Alternative isolation protocols for isolating zein proteins utilize 0.3 M Sodium bisulfite in 10% isopropanol to eliminate possible environmental and health hazards associated with the use of 2-mercaptoethanol.

The natural 27 kDa zein protein contains a total of 2 phenylalanine amino acids. Thus the structural genes encoding the 27 kDa zein protein are particularly well suited for modification in accordance with the present invention to produce a phenylalanine free protein. Additionally, it is known that the two phenylalanine amino acids subunits are located in a position in the primary structure of the zein protein that participates in forming the globular portion of the protein's secondary structure. Thus the amino acid content of this portion of the natural protein can be modified without affecting the solubility of the zein protein.

Most seed storage proteins are nutritionally incomplete in that they lack one or more of the essential amino acids for proper nutrition of higher animals including humans. It is a further object of the present invention to increase the nutritional value of native storage proteins by modifying the nucleic acid sequence of genes encoding the proteins. For the purpose of this invention "increasing the nutritional value" of a protein is defined as altering the ratio of amino acids present in the protein by increasing the content of non-phenylalanine amino acid residues that are underrepresented in the native protein. For example the natural 27 kDa zein protein lacks the essential amino acids lysine and tryptophan. In accordance with the present invention the gene encoding this protein can be modified to increase the content of lysine and tryptophan in the encoded protein. In particular, the nutritional content of the phenylalanine free proteins of the present invention can be enhanced by further modifying the sequence of the modified gene encoding the protein to increase the content of non-phenylalanine essential amino acids underrepresented in the natural protein. Alternatively, the nucleic acid sequence of the natural gene can be modified to simultaneously remove phenylalanine codons and increase the nutritional value of the protein, by modifying the phenylalanine codons to amino acid codons underrepresented in the natural gene.

Once the gene has been modified to reduce or eliminate phenylalanine encoding sequences from the reading frame of the gene, the modified gene can be inserted into commercially available DNA vectors (expression vectors) to express the encoded gene protein product. These expression vectors have promoter sequences and other regulatory sequences necessary for expression in host cells. The technique of using expression vectors to synthesize exogenous genes in a host cell is well known to those familiar with the art. For example the expression vector pET21a is commercially available and can be used to express proteins in *E. coli*.

Once the modified structural gene has been subcloned into an expression vector, the resulting plasmid can be used to transform a host cell, using procedures known to those familiar with the art. The transformed host cells will then synthesize the modified protein which can be isolated and purified using standard methods known to those familiar with the art.

Host cells may be selected from any cell in which expression of modified proteins can be made compatible, including bacteria, fungus, yeast, plant cells and animal cells. Preferred host cells include prokaryotes selected from the genus Escherichia and eukaryotes selected from the genus Pichia.

EXAMPLE 1

The Altered Sites™ in vitro mutagenesis system can be used to efficiently produce mutations in DNA sequences (consistent mutation frequencies of 80% or better have been obtained). The Altered Sites™ in vitro mutagenesis system (see FIG. 1) consists of a mutagenesis vector and a procedure for the selection of oligonucleotide-directed mutants. The system is based on the use of a second mutagenic oligonucleotide to confer antibiotic resistance to the synthesized mutant DNA strand. The system employs a phagemid (a DNA vector capable of replicating either as a plasmid or as a phage), the pALTER™-1 vector, which contains two genes for antibiotic resistance. One of these genes encodes tetracycline resistance and is always functional, whereas the other gene encodes ampicillin resistance and is inactivated. An oligonucleotide (called the ampicillin repair oligo hereafter) is provided which restores ampicillin resistance to the mutant strand during the mutagenesis reaction.

After the DNA sequence to be mutagenized has been cloned into the double stranded pALTER™ vector and used to transform *E. coli* cells, the transformed cells are infected with a helper phage to induce phage replication and the production of single stranded DNA (ssDNA). A mutagenic oligonucleotide is prepared which is complementary in all but a few base pairs (those that are to be changed) of the DNA sequence to be modified. The mutagenic oligonucleotide and the ampicillin repair oligo are annealed to the single-stranded DNA (ssDNA) template at the same time, and subsequent DNA synthesis and ligation of the mutant strand links the two oligonucleotides.

The newly formed double stranded DNA, containing DNA mismatches at the site where the two oligonucleotides were annealed, is then transformed into a repair minus strain of *E coli* (BMH 71-18 mutS) and the cells are grown in the presence of ampicillin, yielding large numbers of colonies. A second round of transformation in JM109 or a similar host ensures proper segregation of mutant and wild type plasmids and results in a high proportion of mutants.

The Altered Sites™ in vitro mutagenesis system includes a positive control vector and oligonucleotide which can be used to check the efficiency of the system using a white/blue assay for mutants. The pALTER-Control vector contains a four base deletion which removes the PstI site from the polylinker and disrupts lacZ function, resulting in white colonies on indicator plates. The lacZ control oligonucleotide restores the PstI site and lacZ function, yielding blue colonies.

EXAMPLE 2

The native γ zein gene was initially cloned as a 5.7 kb SalI/SalI fragment ligated into the SalI site of the pGEM3Z vector (commercially available from Promega, Madison, Wis.) to generate clone GZN0. The native γ zein gene was then subcloned, by digesting GZN0 with restriction endonucleases SalI and EcoRI and ligating the SalI/EcoRI fragment into the in vitro mutagenesis vector pALTER™, (commercially available from Promega, Madison, Wis.) to produce the plasmid GZN1.

All mutations to the native zein gene were created using the site directed mutatgenetic procedure described in Example 1. A summary of clones generated from in vitro mutagenesis is provided in FIG. 2. The GZN1 subclone was modified to create two new EcoRI sites flanking the coding sequence of the native zein gene to produce plasmid MGZN4. These two new EcoRI sites were constructed by mutating bases 3, 4, 5 of the native gene (See Seq ID NO:1) using the oligonucleotide represented by Seq ID NO:3 to change the sequence GACACC to GAATTC, which encodes the 5' EcoRI site, and bases 832 (T→A) and 836 (G→C) using the oligonucleotide represented by Seq ID NO:4 to produce the terminal 3' EcoRI site. The EcoRI/EcoRI fragment encoding the zein protein was subcloned into the pALTER™ vector to create GZN10.

EXAMPLE 3

Plasmid GZN10 can be further modified to alter the coding sequence of the zein gene to eliminate phenylalanine from the encoded protein. The first of two phenylalanine amino acid residues can be altered to isoleucine through the use of an oligonucleotide that changes bases at 397 (T→A) and 399 (T→C). The second phenylalanine residue can then be changed to isoleucine through the use of an oligonucleotide that changes base 520 (T→A). The modified zein protein encoded by this plasmid would be identical in amino acid sequence to the native zein protein except the phenylalanine amino acid residues would be replaced with isoleucine.

EXAMPLE 4

Figure 3:
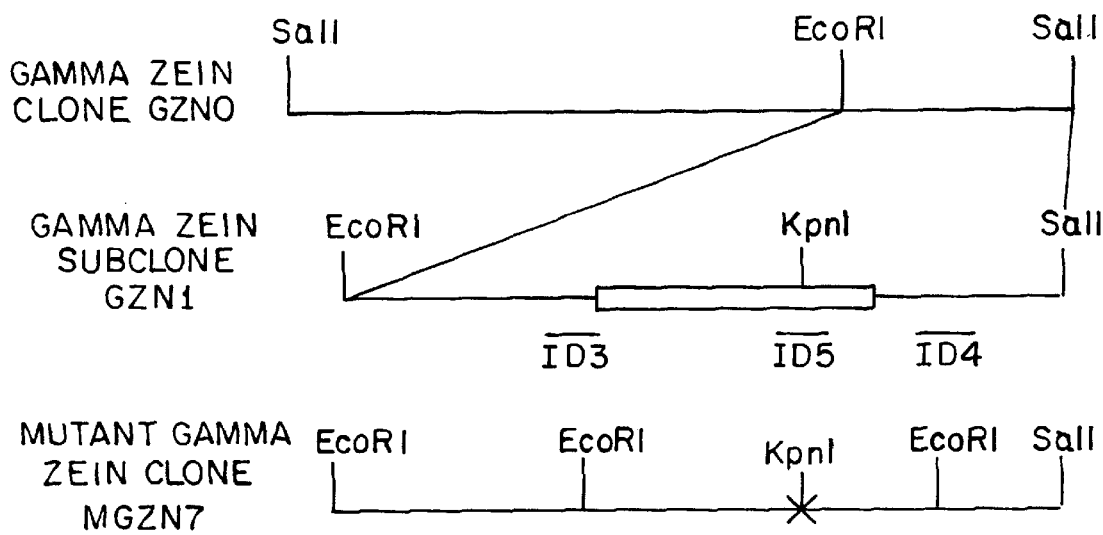
FIG. 3 depicts the generation of gamma zein clone MGZN7. The genomic gamma zein 5.7 kb clone, GZN0, was digested with EcoRI and SalI to release a 1.7 kb fragment containing the coding region and the 5' untranslated region (UTR) of the gamma zein gene. This 1.7 kb fragment was subcloned into the pALTER-1 ampicillin sensitive (amp$^S$), tetracycline resistant (tet$^R$) vector to produce clone GZN1. Clone MGZN7 was produced by inclusion of the three mutagenic oligonucleotides (Seq ID NOS. 3, 4, and 5) and the ampicillin repair oligonucleotide in one in vitro mutagenesis reaction.

The zein gene encoded by clone GZN1 was further modified using a combination of three oligonucleotides (Seq ID NOS:3, 4 and 5) to create two new EcoRI sites flanking the coding sequence of the native zein gene and replace the second of the two phenylalanine codons with a codon for isoleucine. The resulting clone containing this mutated gene is designated MGZN7 (see FIG. 3).

Figure 4:
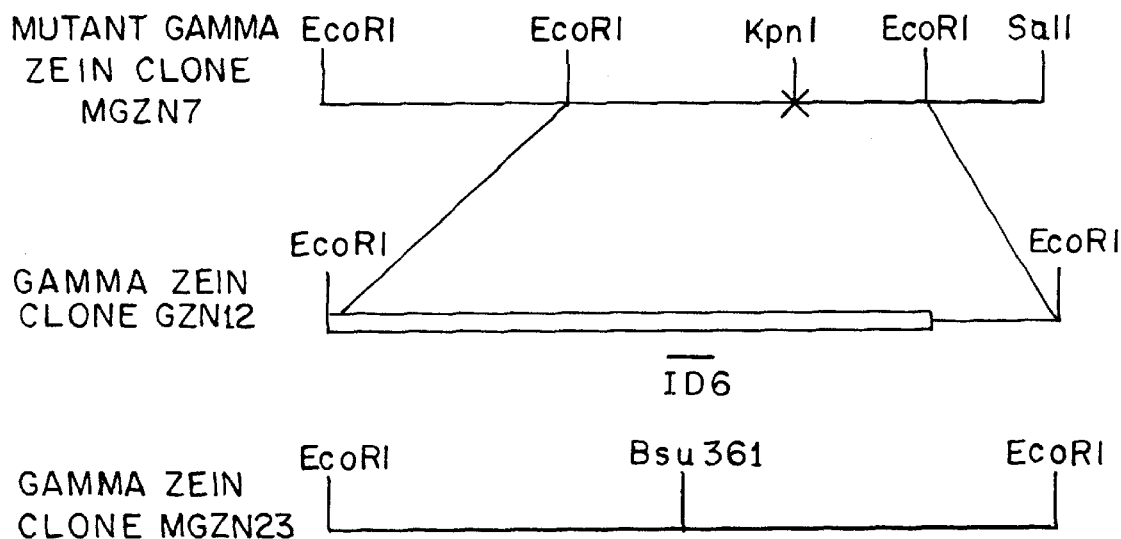
FIG. 4 depicts the generation of gamma zein clone MGZN23. Clone MGZN7 was digested with EcoRI to release the 0.83 kb gamma zein coding region and cloned into the pALTER-1 ampicillin sensitive (amp$^S$), tetracycline resistant (tet$^R$) vector to produce clone GZN12. Clone MGZN23, having the two phenylalanine codons eliminated, was created through mutagenesis using GZN12 ssDNA and a mutagenic oligonucleotide (Seq ID NO 6).

The MGZN7 clone was digested with the restriction enzyme EcoRI and the EcoRI/EcoRI fragment encoding the zein protein was subcloned into the pALTER™ vector to create GZN12. The zein encoding sequence of GZN12 was then modified, using the oligonucleotide represented by Seq ID NO:6 to replace the remaining phenylalanine codon with a codon for isoleucine. The plasmid encoding this modified zein gene is designated MGZN23 (see FIG. 4).

The modified zein gene encoded by clone MGZN23 (represented by Seq ID NO:2) contains base changes at residues 3 (C→A), 4 (A→T), 5 (C→T), 397 (T→A) and 399 (T→C) 406 (C→T), 414 (C→G), 418 (C→A), 419 (C→A), 511 (C→A), 520 (T→A), 529 (G→A), and 532 (C→A) 829 (T→A) and 833 (G→C). The mutation at base 511 modifies the KpnI recognition sequence resulting in the loss of KpnI's ability to cleave the sequence, and the base change at base 399 introduces a new Bsu36I restriction site. These mutations in addition to removing phenylalanine from the encoded protein also improve the quality of the encoded protein for human PKU patient nutrition by increasing the lysine content by two, isoleucine content by five, tryptophan content by two, and tyrosine content by one. This is particularly important since the natural zein protein does not contain lysine or tryptophan.

EXAMPLE 5

The presence of the desired mutations in the zein gene has been demonstrated by reconstructed endonuclease cleavage of the vectors bearing the inserts. The presence of cleavage sites for EcoRI and Bsu36I demonstrates the introduction of the terminal sites of the gene and the elimination of one of the phenylalanine codons. The loss of sensitivity to KpnI indicates the loss of one amino acid, lysine, whose single codon was changed through the use of a mutagenic primer which also carried the mutation eliminating the phenylalanine codon beginning at base pair 520–522. The presence of the mutations removing the phenylalanine codons has been further verified by nucleic acid dideoxy sequence analysis.

EXAMPLE 6

The expression of the Phenylalanine free modified natural proteins were produced using an *E.coli* host and the *E.coli* expression vector, pET21a (Novagen, see FIG. 2). The expression of these modified genes could be determined by an assay utilizing the T7●Tag Antibody. The T7●Tag Antibody is a mouse monoclonal antibody (subclass $IgG_{2b}$, k) directed against the 11 amino acid gene 10 leader peptide expressed by the pET expression vectors. Target genes cloned into the multiple cloning site of these vectors express proteins carrying the leader peptide fused to their amino terminal end. The peptide (Met-Ala-Ser-Met-Thr-Gly-Gly-Gln-Gln-Met-Gly) is the natural amino terminal end of the T7 major capsid protein. Since the antibody reacts specifically with this peptide, it can be used as an epitope tag to follow target proteins by sensitive immunological procedures.

Target genes cloned in pET vectors are commonly expressed by transforming recombinant plasmids into strains that are lysogenic for bacteriophage λDE3. Such strains carry a chromosomal copy of the T7 RNA polymerase gene under the control of the lacUV5 promoter. Target protein expression is induced by the addition of IPTG to a growing culture, which allows production of T7 RNA polymerase and subsequent high-level transcription of target gene sequences from the T7 promoter. Detailed protocols for maintenance and induction of pET recombinants are described in commercially available manuals.

The inserts of clones GZN1, GZN12, and MGZN23 were each separately subcloned into the *E.coli* expression vector, pET21a. *E.coli* cells were transformed with the pET21a constructs and the native and mutant zein proteins were expressed after being induced in the presence of IPTG. *E.coli* cells containing the EGZN23 plasmid (See FIG. 2) express a phenylalanine free zein protein, and this cell line is designated as *E.coli* GZPKU23. The presence of the expressed proteins was detected using antibodies directed against both the natural protein as well as the amino terminal T7 gene 10 protein tag.

I claim:

1. A method for minimizing the physiological symptoms of phenylketonuria in PKU individuals, said method comprising the step of administering to said individual a dietary composition comprising an intact, modified gamma zein protein, wherein the modifications to the protein include removing all phenylalanine amino acids.

2. An improved dietary composition for administration to patients having PKU, said composition comprising an intact gamma zein protein encoded by a gamma zein gene modified to eliminate the phenylalanine codons from the coding sequence of said gene.

3. A modified gene encoding for a gamma zein protein, said gene having been modified to remove phenylalanine codons from the reading frame of said gene.

4. The modified gamma zein gene of claim 3 having the nucleic acid sequence as set forth in Seq ID NO:2.

5. The modified gene of claim 3 wherein the phenylalanine codons of the natural gene have been altered to encode for amino acids underrepresented in the natural protein.

6. The modified gene of claim 5 wherein the phenylalanine codons have been altered to encode amino acids selected from the group consisting of lysine and tryptophan.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 836 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Zea mays (vii) IMMEDIATE SOURCE:
       (B) CLONE: GZN1

(xi) SEQUENCE DESCRIPTION: SEQ ID NO:1:

| | | | | | |
|---|---|---|---|---|---|
| GACACCATGA | GGGTGTTGCT | CGTTGCCCTC | GCTCTCCTGG | CTCTCGCTGC | GAGCGCCACC | 60 |
| TCCACGCATA | CAAGCGGCGG | CTGCGGCTGC | CAGCCACCGC | CGCCGGTTCA | TCTACCGCCG | 120 |
| CCGGTGCATC | TGCCACCTCC | GGTTCACCTG | CCACCTCCGG | TGCATCTCCC | ACCGCCGGTC | 180 |
| CACCTGCCGC | CGCCGGTCCA | CCTGCCACCG | CCGGTCCATG | TGCCGCCGCC | GGTTCATCTG | 240 |
| CCGCCGCCAC | CATGCCACTA | CCCTACTCAA | CCGCCCCGGC | CTCAGCCTCA | TCCCCAGCCA | 300 |
| CACCCATGCC | CGTGCCAACA | GCCGCATCCA | AGCCCGTGCC | AGCTGCAGGG | AACCTGCGGC | 360 |
| GTTGGCAGCA | CCCCGATCCT | GGGCCAGTGC | GTCGAGTTTC | TGAGGCATCA | GTGCAGCCCG | 420 |
| ACGGCGACGC | CCTACTGCTC | GCCTCAGTGC | CAGTCGTTGC | GGCAGCAGTG | TTGCCAGCAG | 480 |
| CTCAGGCAGG | TGGAGCCGCA | GCACCGGTAC | CAGGCGATCT | TCGGCTTGGT | CCTCCAGTCC | 540 |
| ATCCTGCAGC | AGCAGCCGCA | AAGCGGCCAG | GTCGCGGGGC | TGTTGGCGGC | GCAGATAGCG | 600 |
| CAGCAACTGA | CGGCGATGTG | CGGCCTGCAG | CAGCCGACTC | CATGCCCCTA | CGCTGCTGCC | 660 |
| GGCGGTGTCC | CCCACTGAAG | AAACTATGTG | CTGTAGTATA | GCCGCTGGCT | AGCTAGCTAG | 720 |
| TTGAGTCATT | TAGCGGCGAT | GATTGAGTAA | TAATGTGTCA | CGCATCACCA | TGGGTGGCAG | 780 |
| TGTCAGTGTG | AGCAATGACC | TGAATGAACA | ATTGAAATGA | AAGAAAAAA | GTATTG | 836 |

(2) INFORMATION FOR SEQ ID NO:2:

(i) SEQUENCE CHARACTERISTICS:
       (A) LENGTH: 836 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Zea mays (vii) IMMEDIATE SOURCE:
       (B) CLONE: MGZN23

(xi) SEQUENCE DESCRIPTION: SEQ ID NO:2:

```
GAATTCATGA GGGTGTTGCT CGTTGCCCTC GCTCTCCTGG CTCTCGCTGC GAGCGCCACC      60

TCCACGCATA CAAGCGGCGG CTGCGGCTGC CAGCCACCGC CGCCGGTTCA TCTACCGCCG     120

CCGGTGCATC TGCCACCTCC GGTTCACCTG CCACCTCCGG TGCATCTCCC ACCGCCGGTC     180

CACCTGCCGC CGCCGGTCCA CCTGCCACCG CCGGTCCATG TGCCGCCGCC GGTTCATCTG     240

CCGCCGCCAC CATGCCACTA CCCTACTCAA CCGCCCCGGC CTCAGCCTCA TCCCCAGCCA     300

CACCCATGCC CGTGCCAACA GCCGCATCCA AGCCCGTGCC AGCTGCAGGG AACCTGCGGC     360

GTTGGCAGCA CCCCGATCCT GGGCCAGTGC GTCGAGATCC TGAGGTATCA GTGGAGCAAG     420

ACGGCGACGC CCTACTGGTC GCCTCAGTGC CAGTCGTTGC GGCAGCAGTG TTGCCAGCAG     480

CTCAGGCAGG TGGAGCCGCA GCACCGGTAC AAGGCGATCA TCGGCTTGAT CATCCAGTCC     540

ATCCTGCAGC AGCAGCCGCA AAGCGGCCAG GTCGCGGGGC TGTTGGCGGC GCAGATAGCG     600

CAGCAACTGA CGGCGATGTG CGGCCTGCAG CAGCCGACTC CATGCCCCTA CGCTGCTGCC     660

GGCGGTGTCC CCCACTGAAG AAACTATGTG CTGTAGTATA GCCGCTGGCT AGCTAGCTAG     720

TTGAGTCATT TAGCGGCGAT GATTGAGTAA TAATGTGTCA CGCATCACCA TGGGTGGCAG     780

TGTCAGTGTG AGCAATGACC TGAATGAACA ATTGAAATGA AAGAAAAAA GAATTC         836
```

(2) INFORMATION FOR SEQ ID NO:3:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

```
GAAGAACCCG ATCGAATTCA TGAGGGTGTT GC                                    32
```

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

```
TGAAAAGAAA AAAGAATTCT TCCAAATTAA ACG                                   33
```

(2) INFORMATION FOR SEQ ID NO:5:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO

```
        (iv) ANTI-SENSE: NO (xi) SEQUENCE DESCRIPTION: SEQ ID NO:5:

GCAGCACCGG TACAAGGCGA TCATCGGCTT GATCATCC                                    38

(2) INFORMATION FOR SEQ ID NO:6:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

GGCCAGTGCG TCGAGATCCT GAGGTATCAG TGGAGCAAGA CGGCGACG                         48
```